(12) United States Patent
Vito (10) Patent No.: US 6,595,206 B2
(45) Date of Patent: Jul. 22, 2003

(54) EXTENDABLE SPACER DEVICE AND METERED DOSE INHALER

(76) Inventor: John Vito, 519 School St., Clarks Summit, PA (US) 18411

( * ) Notice: Subject to any disclaimer, the term of this patent is extended or adjusted under 35 U.S.C. 154(b) by 0 days.

(21) Appl. No.: 10/272,237

(22) Filed: Oct. 16, 2002

(65) Prior Publication Data

US 2003/0029447 A1 Feb. 13, 2003

Related U.S. Application Data

(63) Continuation-in-part of application No. 09/904,701, filed on Jul. 13, 2001, now abandoned.

(51) Int. Cl.[7] ............................................. A61M 11/00
(52) U.S. Cl. ........................ 128/200.23; 128/200.12
(58) Field of Search ....................... 128/200.11, 200.12, 128/200.14, 200.22, 200.23, 203.12, 203.15, 203.18, 203.21, 203.19, 205.24, 202.27, 200.21; 604/57.58

(56) References Cited

U.S. PATENT DOCUMENTS

| | | | |
|---|---|---|---|
| 2,865,370 A | | 12/1958 | Gattone |
| 3,001,524 A | | 9/1961 | Maison et al. |
| 3,998,226 A | | 12/1976 | Harris |
| 4,292,966 A | * | 10/1981 | Mono et al. ............ 128/200.23 |
| 4,470,412 A | * | 9/1984 | Nowacki et al. ........ 128/200.18 |
| 4,637,528 A | * | 1/1987 | Wachinski et al. ........... 222/182 |
| 4,641,644 A | * | 2/1987 | Andersson et al. .... 128/200.23 |
| 4,953,545 A | | 9/1990 | McCarty |
| 5,012,803 A | | 5/1991 | Foley et al. |
| 5,074,294 A | | 12/1991 | Chiesi |
| 5,178,138 A | * | 1/1993 | Walstrom et al. ....... 128/200.23 |
| 5,203,323 A | * | 4/1993 | Tritle ..................... 128/200.23 |
| 5,318,016 A | * | 6/1994 | Mecikalski ............. 128/200.23 |
| 5,368,016 A | | 11/1994 | Henry |
| 5,427,089 A | * | 6/1995 | Kraemer ................. 128/200.23 |
| 5,431,154 A | * | 7/1995 | Seigel et al. ............ 128/200.14 |
| 5,477,849 A | * | 12/1995 | Fry ......................... 128/200.14 |
| 5,505,194 A | * | 4/1996 | Adjei et al. ............ 128/200.23 |
| 5,507,278 A | | 4/1996 | Karell |
| 5,676,130 A | * | 10/1997 | Gupte et al. ........... 128/203.19 |
| 5,746,197 A | | 5/1998 | Williams |
| 5,809,996 A | | 9/1998 | Alldredge |
| 6,014,972 A | * | 1/2000 | Sladek .................... 128/203.12 |
| 6,039,042 A | * | 3/2000 | Sladek .................... 128/200.23 |
| 6,073,629 A | * | 6/2000 | Hardy et al. ............ 128/203.15 |
| 6,202,643 B1 | * | 3/2001 | Sladek .................... 128/200.23 |
| 6,257,231 B1 | * | 7/2001 | Shick et al. ............. 128/200.14 |
| 6,293,279 B1 | * | 9/2001 | Schmidt et al. ......... 128/200.23 |
| 6,341,603 B1 | * | 1/2002 | Howlett .................. 128/200.23 |
| 6,363,932 B1 | * | 4/2002 | Forchione et al. ...... 128/203.12 |
| 6,394,085 B1 | * | 5/2002 | Hardy et al. ............ 128/203.15 |
| 6,415,785 B1 | * | 7/2002 | Stage ...................... 128/200.23 |
| 6,435,176 B1 | * | 8/2002 | Berg et al. .............. 128/200.23 |
| 6,435,177 B1 | * | 8/2002 | Schmidt et al. ......... 128/200.23 |

FOREIGN PATENT DOCUMENTS

| | | |
|---|---|---|
| EP | 0015247 | 1/1980 |
| EP | 0074937 | 7/1982 |
| GB | 2110543 | 12/1981 |
| GB | 21282249 | 5/1987 |

* cited by examiner

*Primary Examiner*—Weilun Lo
*Assistant Examiner*—Teena Mitchell
(74) *Attorney, Agent, or Firm*—Kenneth P. Glynn, Esq.

(57) ABSTRACT

The present invention is directed to a metered dosage inhaler device having a main housing member for receiving and dispensing inhalation medication that is hollow, and has an aerosol medication container insertion end and a nozzle portion, wherein the nozzle has a defined length and has an orifice with a defined cross-sectional area outlet surfaces and inner surfaces. There is a spacer member, fitted on the nozzle and adapted to move outwardly and inwardly relatively to the nozzle, the spacer being hollow and being located about either outer surfaces or within the inner surfaces of the nozzle, the spacer having a total length about equal to or less than the nozzle when on the outside, or at least half of its length within the device when on the inside, so as to preserve significant compactness. The spacer member includes a plurality of movable segments such as telescopic rings, bellows segments or popoid segments.

20 Claims, 6 Drawing Sheets

EXTENDABLE SPACER DEVICE AND METERED DOSE INHALER

REFERENCES TO RELATED APPLICATION

This application is a continuation-in-part of application Ser. No. 9/904,701, filed on Jul. 13, 2001, entitled Extendable Spacer Device For Metered Dose Inhaler, by the same inventor herein, abandoned Oct. 18, 2002.

BACKGROUND OF THE INVENTION

1. Field of the Invention

The present invention inhaler is a metered dose inhaler for medication delivered from aerosol container. It includes an extendable spacer device which extends outwardly and closes inwardly relative to the nozzle inhaler in such a way that the extendable spacer device preserves significant compactness by having a total length about equal to or less than the nozzle length in its contracted form.

2. Information Disclosure Statement

The following patents describe metered dose inhalers with various adaptations, i.e. extendable spacers and related devices:

U.S. Pat. No. 5,809,996 describes an inhalation apparatus that is suited for easily administering aerosol medication via a metered dose pressurized canister. The apparatus has a collapsible tubular body comprised of axially nested rigid pieces including end pieces with opposite connections respectively for directing spray from the canister axially through the tubular body cavity from one connection toward the other connection serving as the users tubular mouthpiece. The tubular body can be axially shifted between an expanded operational position of maximum body cavity volume and maximum separation between the end pieces and a collapsed storage position of maximum separation where the rigid pieces are nested together. The end pieces have end plates of substantially equal size with peripheries suited to be gripped by the user, and a tubular flange projected off of one end plate that cooperates in proximity with structure of the other end plate in the collapsed position, providing a protective housing overlying the rigid pieces when collapsed.

U.S. Pat. No. 5,746,197 describes an extension that is attachable to metered dose inhalers for more effective and efficient delivery of the medication to the lungs of the user. The extension comprises a member having a bore therethrough that is sized and configured at a first end to match the size and shape of the inhaler nozzle, tapers to a reduced cross-section and extends with a generally uniform cross-section for at least one inch to the second end so as to force the user to slowly inhale the medication into the lungs. An adapter attached to the first end of the member receives the nozzle therein so that the nozzle is in fluid is flow communication with the bore of the member. A portion of the member, including the second end, defines a mouthpiece at least one and one half inches long that is receivable in the mouth of a user.

U.S. Pat. No. 5,507,278 describes an inhaler for asthma and other medical conditions which consists of a medicine canister and a canister holder. A tongue guard for the inhaler is attached onto the canister holder, and assists the user in placing the inhaler into the proper position. When the inhaler is activated, flow of medicine is diverted away from the tongue, thereby preventing bad taste and injury to tongue, such as atrophy. It can be used in conjunction with spacer devices or it can be built integrally within canister holder.

U.S. Pat. No. 5,368,016 provides for improved delivery of anaesthetic to an airway. By the invention, topical airway anesthesia is passively provided. A method in accordance with the invention, provides for release of a suitable anaesthetic in aerosolized form from a canister containing the anaesthetic, and utilizes an oropharyngeal airway.

U.S. Pat. No. 5,074,294 describes an apparatus for the administration of drugs in form of metered aerosol, consisting of an expansion chamber comprising two coaxial tubes freely slideable within one another and detachable. The external tube has an open end and a tapered end on which the chamber mouthpiece is mounted. The internal tube has an open end which may be inserted into the external tube and on opposite end on which the mouthpiece of a conventional dispenser containing the active principle in form of pressurized aerosol is stuck. The apparatus allows a better penetration of the drug into the airways up to the deepest zones of the bronchial tree.

U.S. Pat. No. 5,012,803 describes a medical inhaler which has a cylindrical body usable with different inlet and outlet fittings at the opposite ends thereof. An inlet end fitting is provided with inner and outer cylindrical flanges gripping the upstream end of is the cylindrical body and adapted to receive structure for misting medication into said cylindrical body. The downstream or outlet end fittings snaps over the downstream end of the cylindrical body and is provided with an axially extending protrusion impinging against and securing a flexible diaphragm to an inwardly directed flange at the exit end of the cylindrical body. The outlet end fitting may take different forms such as a mouthpiece to fit into a patient's mouth, a mask to fit over a patient's mouth and nose, or a connection for flexible tubing leading to an endotracheal tube.

U.S. Pat. No. 4,953,545 describes a disposable, independent hand-held chamber for the purpose of dispersing aerosol respiratory medication delivered from metered-dose inhalers that comprises an elongated tapered chamber with an aperture on smaller end for insertion of metered-dose inhaler and mouth piece on larger end for inhalation of released aerosol medication.

U.S. Pat. No. 3,998,226 describes an inhalation devise for encapsulated concentrates having a capsule piercing hypodermic needle, a mouthpiece and a cavity for receiving a capsule containing a granular medicant and the like, whereby the device is actuated to pierce the capsule to form a pair of aligned openings. An aerosol bottle is so mounted on the device that fluid under pressure is conducted through the hypodermic needle and through the aligned openings in the capsule to disperse particles of the medicant thereby. The mixture of fluid under pressure and particles of medicant are then discharged through a venturi passageway in the mouthpiece and into a person's mouth.

U.S. Pat. No. 3,001,524 is directed to a device suitable for use in combination with an aerosol dispensing container equipped with a metering valve means and charged with a medicament-containing, self-propelling liquid composition, which comprises in combination an aerosol dispensing container charged with a medicament-containing, self-propelling liquid composition and equipped with metering valve, and a means for actuating said metering valve means and a delivery tube member so shaped and so proportioned as to conform to an oral cavity of the user and capable of administering into a body cavity a measured dose of medicament in aerosol form substantially free of droplets of unvaporized, liquid propellant to accomplish inhalation therapy, said actuating means being equipped with air inlet means between it and said dispensing container permitting scavenging of the medicament-containing aerosol from the tube into the body cavity of the user, said delivery tube member being of substantially straight longitudinal axis and of sufficient length to deliver a dose of medicament substantially free of unvaporized liquid propellant while preventing substantial loss of medicament-containing aerosol, said device being small enough to transport in the pocket of the user, said container and said actuating means being usable in detachable engagement with each other.

U.S. Pat. No. 2,865,370 describes a dispensing adapter for use with disposable is aerosol units having a hollow valve stem, comprising a hollow body formed with a coupling skirt, a centrally apertured plate mounted in the body above the skirt engagable over the valve stem, valve operating means carried by the body positioned above the end of the valve stem, and a discharge nozzle extending from the said body, said valve operating means including a curved surface, said surface being directed toward the discharge end of said discharge nozzle by index means formed in said aerosol units and said skirt portion of the body.

U.K. Patent No. 2,182,249 describes a compressible nebuhaler which has a spindle shaped, transparent polythane bag like the bellows of an accordion which is attached at either end to the centers of circular discs and encircling the openings of the mouthpiece and the opening for the insertion of an aerosol. Aerial like or "telescopic" metallic rods around the spindle shaped compressible chamber expand or compress the nebuhaler chamber by lengthening or shortening when appropriate pressure is applied.

The compressed nebuhaler has a shape of a "burger" and can easily be carried in a vanity bag or school bag.

U.K. Patent No. 2,110,543 describes an inhalation chamber for use with a supply of aerosol-propelled medication, comprises a mouthpiece 15 and a set of clear plastics, telescoping rings 7A to 7J, and 6, which define, in their extended position, the inhalation chamber. The inhalation chamber through the smallest ring 7A e.g. from an aerosol. The user may then draw on the mouthpiece 15 to open a non-return valve in an end wall 5 of the chamber, and inhale the medication.

The chamber may be collapsed, the rings then adopting their nested position within a casing formed by the end wall 5 and the outermost ring 6. A detachable cover is engaged over the open end of the latter. The inhaler components may thus, fit readily into the user's pocket or handbag.

U.K. Patent No. 0,074,937 describes an aerosol inhalation device in pocket size which has on dosage dispensing position and one storage position, and which comprises a two part telescoping deceleration chamber with rectangular cross section and a socket for an exchangeable aerosol container. The socket is connected with the inner chamber part so that it can be telescopically inserted therein to form a storage position. In dosage dispensing position the socket is extended from the deceleration chamber, pivoted at an angle relative the longitudinal axis of the chamber and locked in said angle.

U.KS. Patent No. 0,015,247 describes an aerosol inhalation device comprising an elongated chamber, an outer chamber part of which has an outlet opening and is telescopically displaceable over an inner chamber part which is connectable to an aerosol dispenser and provided with a flexible tongue which on telescoping the device together closes the outlet opening.

Notwithstanding the prior art, the present invention is neither taught nor rendered obvious thereby.

SUMMARY OF THE INVENTION

The present invention relates to a metered dosage inhaler device having a main housing member for receiving and dispensing inhalation medication, the main housing member being hollow, and having an aerosol medication container insertion end and a central axis of direction of insertion of an aerosol medication container and having a nozzle portion for spraying medication into a mouth of a user. The nozzle portion includes a nozzle segment that is exterior from the main housing member and has a defined length L, as well as, an orifice with a defined cross-sectional area, outer surfaces and inner surfaces.

There is also a spacer member fitted on the nozzle segment that is adapted to move outwardly and inwardly relatively to the nozzle segment, the spacer member being hollow and being located about the outer surfaces of said nozzle segment, or located within the inner surfaces of the nozzle segment. The spacer member, when closed, has a total length about or equal to or less than the nozzle segment L, so as to preserve significant compactness when the spacer is moved inwardly relative to the nozzle. When opened, the spacer member extends outwardly via interconnected, moveable segments, the outermost (i.e. extended most) segment also functions as a mouthpiece.

In some preferred embodiments, the spacer member plurality of movable segments may be, for example, interlocking collapsible, telescopic rings. Alternatively, they may be bellow segments or popoid segments.

In other embodiments of the present invention, there is also a divider wafer located within the inhaler main housing member, located between the aerosol container nesting and the nozzle portion, to prevent a user from blowing medication out the container insertion end. The divider wafer also includes a one-way valve to permit air to be taken from the container insertion end to nozzle segment by a user, but not vice-versa.

BRIEF DESCRIPTION OF THE DRAWINGS

The present invention should be more fully understood when the specification herein is taken in conjunction with the drawings appended hereto wherein.

DETAILED DESCRIPTION OF THE PRESENT INVENTION

Figures 1, 2:
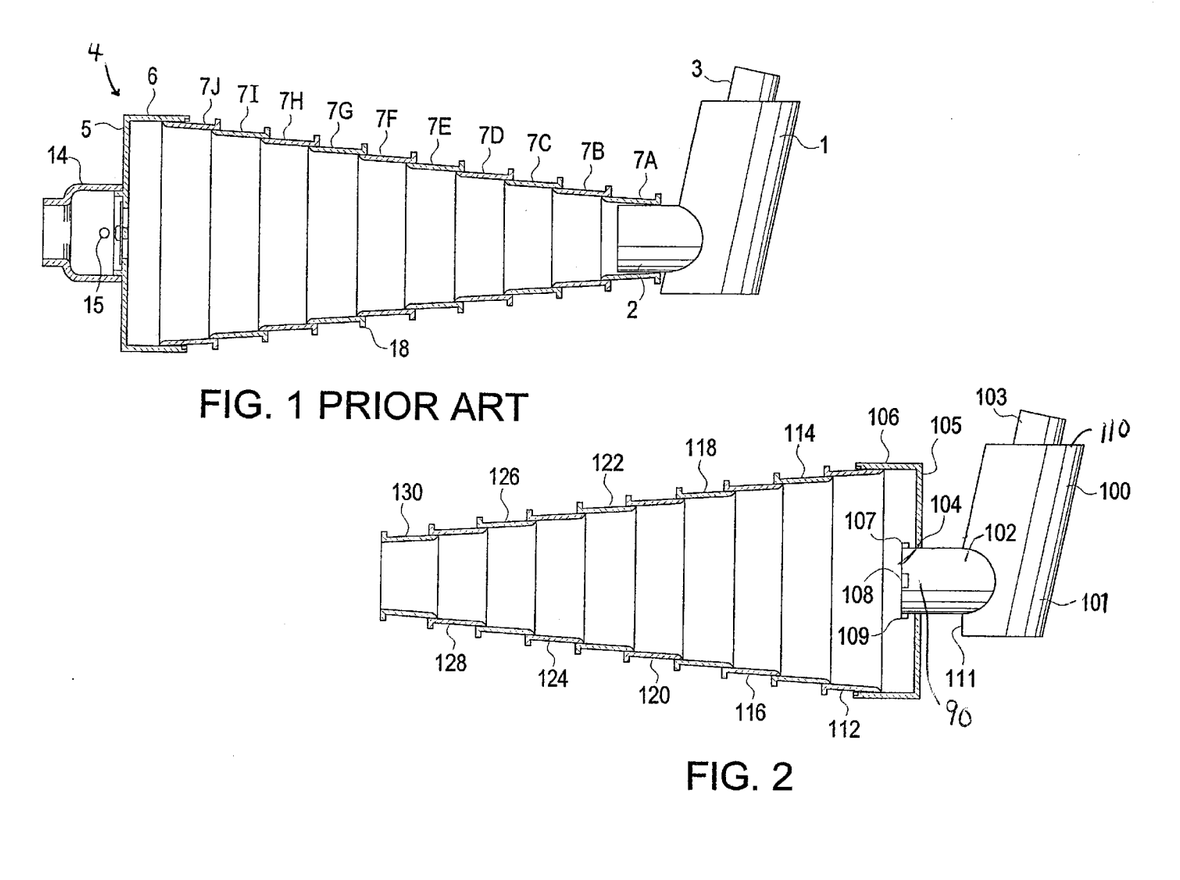
FIGS. 1 and 3 illustrate side views of a prior art inhaler device with a telescopic spacer.
FIGS. 2 and 4 show side views of a present invention metered dose inhaler device with a telescopic spacer member in its extended and retracted modes, respectfully.
Figure 3:
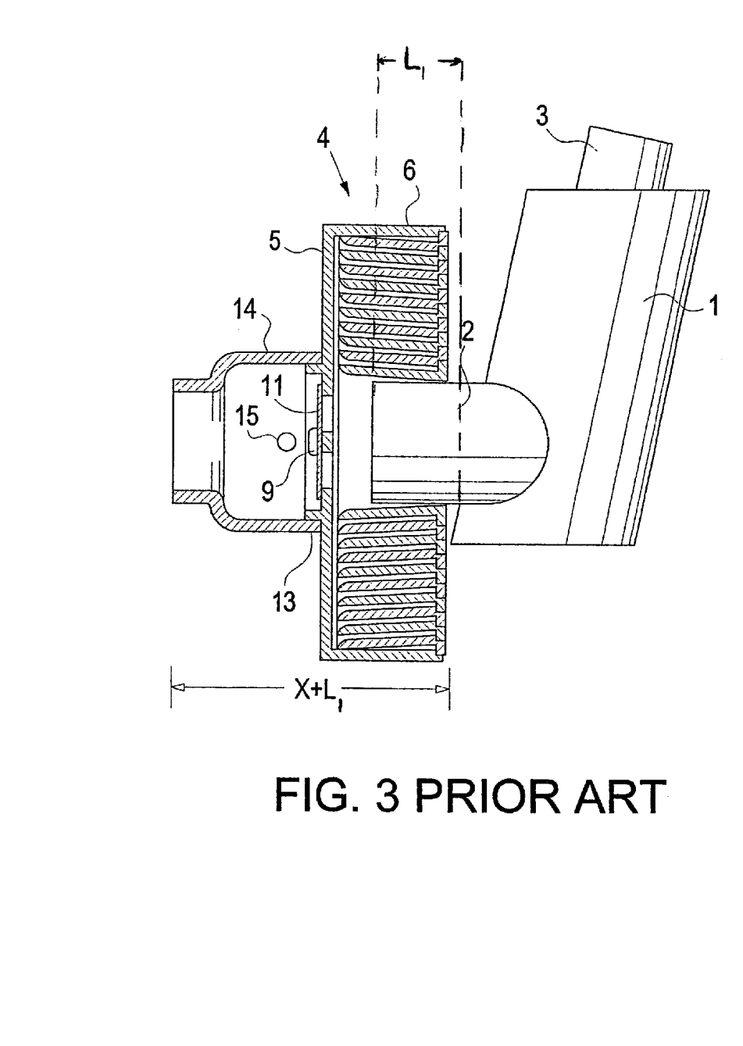
Figure 4:
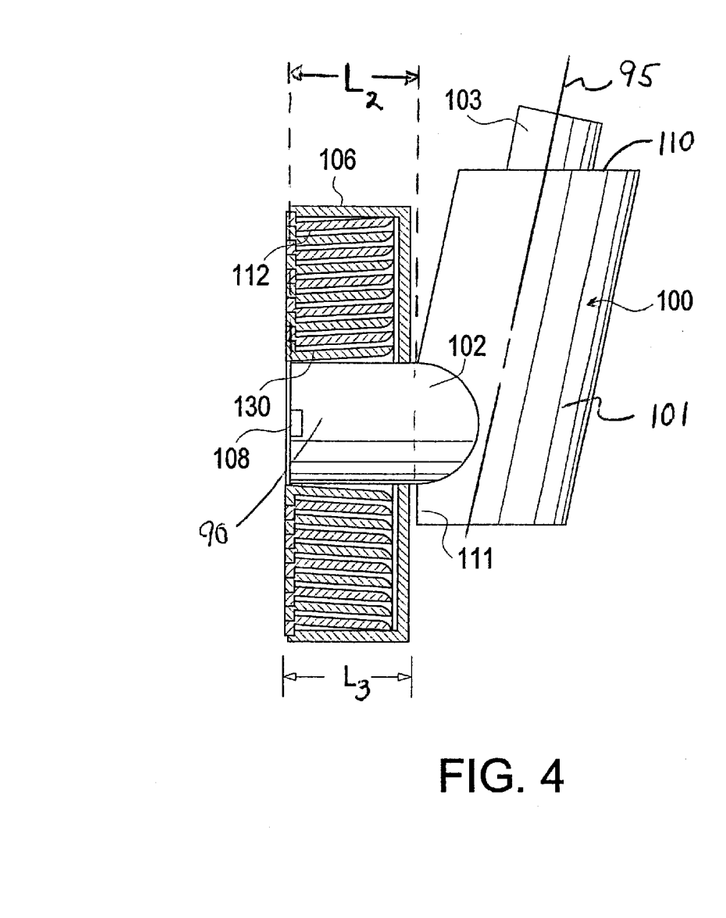

FIGS. 1 and 3 show prior art metered dose inhalers with spacer adaptations and FIGS. 2 and 4 show present invention metered dose inhalers with compacted extendable spacer adaptations.

Identical parts in FIGS. 1 and 3 are identically and, likewise, identical part in FIGS. 2 and 4 are identically numbered. The prior are inhaler shown in FIGS. 1 and 3 is shown in extended and retracted modes, respectfully, and comprises a conventional handheld pocket-size inhaler having a main housing body 1 and an outlet nozzle segment 2 which can be used directly as a dispersion chamber assembly or have an appropriately shaped mouthpiece spacer 4 attached to it, and an aerosol canister 3 inserted into the body 1. When canister 3 is pushed downwardly (as seen in FIG. 1) to open the valve of the aerosol canister 3, a mixture of drug and propellant is ejected from the outlet nozzle segment 2.

A dispersion chamber assembly spacer 4 is shown in its extended condition in FIG. 1 and its retracted position in FIG. 3. The dispersion chamber assembly spacer 4 comprises and end wall 5 with which is integrally molded the outermost ring 6 of a set of telescopically nested rings 7A to 7J. Each ring 7 is frusto-conical with the angle of taper of both its inner and its outer walls to the axis, as shown. As can be seen in the FIG. 2, the end marginal portion of the outer surface of the larger and of each ring makes jamming contact with the end marginal portion of the inner surface of the smaller and of the next larger ring in the extended state of the dispersion chamber.

The end wall 5 and each of the rings 7 are conveniently molded from a suitable plastics material, for example transparent polycarbonate, thereby rendering the whole assembly easily washable.

The center of the end wall 5 contains a non-return valve 9 (FIG. 3), formed in this case by openings through a spider portion of the end wall 5 and a rubber disk 11 held captive by a headed pin portion. An annular flange 13 on the end wall 5 forms a detachable mounting for a molded mouthpiece 14 formed with an exhalation outlet hole 15.

As shown in FIG. 1, the larger end of each ring 7 is preferably chamfered or rounded on its inner surface. In order to prevent the smaller rings such as 7A and 7B from falling loosely into the largest rings, it may be found desirable to mold each ring with an outer flange 18 and with an inner rebate to form a seating for the outer periphery of the flange 18 of the next smaller ring.

It will be noted that the dispersion chamber of assembly spacer shown in FIG. 1 in its extended form can readily have a length of 200 mm and a diameter at its larger end of 80 mm but, when packed into its retracted form of figure need only have an overall length, including the flange 13, of only 35 mm. The inner diameter of the smaller ring 7A is sufficient to receive the outlet 2. When the inhaler is in its retracted form, the mouthpiece 14 may be engaged over the upper end of the body 1 and aerosol canister.

While this prior art inhaler shown in FIGS. 1 and 3 with its spacer achieves significant compaction in its retracted form, it still has a significantly increased length as compared to the length of outlet nozzle segment 2. Thus, if the nozzle segment 2 has a length of $L_1$, then the total distance occupied by the nozzle and the spacer would be X plus $L_1$, as shown in FIG. 3, wherein X represents the added length resulting from part of the spacer member extending beyond the nozzle segment 2.

It is an object of the present invention to substantially eliminate, and in preferred embodiments, completely eliminate any added length resulting from a spacer.

Referring to FIGS. 2 and 4, present invention hand held pocket size inhaler 100 includes a main housing member 101 with a medication aerosol container 103 contained therein. This main housing member 101 has an insertion end 110 for receiving and dispensing (pressing) inhalation medication. The container insertion end 110 and the main housing member 101 have a central axis 95 of direction for insertion. The main housing member 101 also includes a nozzle portion 102. Nozzle portion 102 includes a nozzle segment 90 that projects beyond the main housing member 101, and has a length L. Hollow container insertion end 110 includes an extended bottom with a 90 degree corner 111 to enhance compactness as shown in FIG. 4. In FIG. 2, nozzle portion 102 has stops such as 107, 108 and 109 at its nozzle segment distal end 104. These stops prevent wall 105 of telescopic segment 106 from being removed therefrom. Telescopic segment 106 is otherwise slideably mounted on nozzle segment 90 so that it may be slid forward to the aforesaid stops described above and as shown in FIG. 2, or pushed back to corner 111 as shown in FIG. 4. Likewise, annular segments 112, 114, 116, 118, 120, 122, 124, 126, 128 and 130 are extendable and retractable in a fashion similar to those shown in FIGS. 1 and 3 and have similar stop arrangements, except that smallest annular segment 130 also functions as the mouthpiece for the inhaler user. As can be seen in FIG. 4, in its retracted mode, the total length of the spacer member $L_3$ is equal to, or less then $L_2$ then length of the nozzle segment 90.

It should be noted that FIGS. 2 & 4 show an extreme version of the present invention so that a clear comparison could be made between the present invention and prior art. However, in many viable versions of the present invention, the number of segments would be far fewer then those shown in FIGS. 2 and 4. For example, embodiments having only 2 or 3 segments such as shown and described below in FIGS. 5 and 7.

Figures 5, 6:
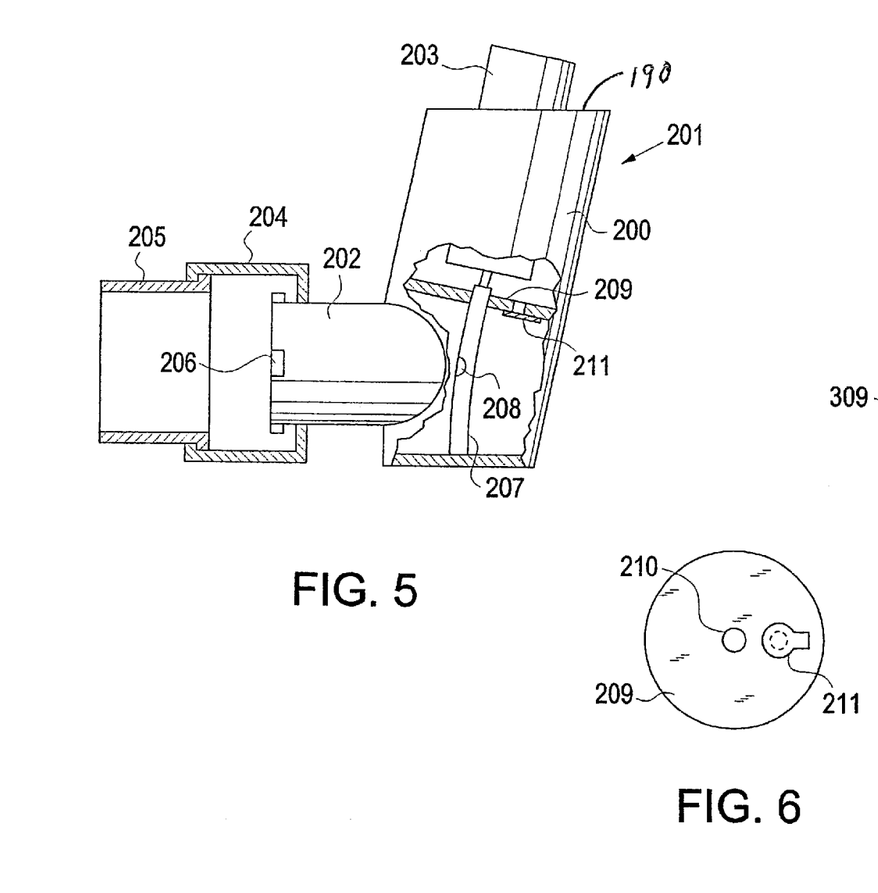
FIG. 5 shows a side, partially cut view of an alternative embodiment present invention metered dose inhaler device with a disk divider.
FIG. 6 shows a bottom view of the disk divider.

Referring now to FIGS. 5 and 6 there is shown an inhaler 201 with a medication container receiving section end 190 of housing member 200 and a nozzle 202. This nozzle 202 has a nozzle segment, which is the segment of nozzle 202 extending beyond. The nozzle has stops, such as stop 206, that maintain segment 204 so as to be slideably movable with respect to nozzle 202, but not removable therefrom. Mouthpiece segment 205 is slideably movable within segment 204 and has sufficient inner-diameter to fit over nozzle 202 when both segments are compressed (retracted) medication container receiving section 200 is partially cut open to show its hollow interior with injector stem 207. Stem 207 has a hollow top for receiving the release valve of medication container 203 such that, when medication container 203 is pressed downwardly pressurized medication is released and exits at orifice 208 to spray outwardly through nozzle 202 and segments 204 and 205.

Referring to both FIGS. 5 and 6, disk divider 209 is shown. It is located within the main housing member 200 toward the medication container receiving end 190 above orifice 208 and nozzle 202. Thus, it is below medication container 203 and includes orifice 210 fitted to stem 207. It has a one way valve 211 which permits air to be pulled downwardly form the upper portion of medication container receiving section 200 into its lower portion, nozzle 202 and segments 204 and 205 for inhalation, but not vice versa. This prevents the user from blowing away medication inadvertently or intentionally.

Figure 7:
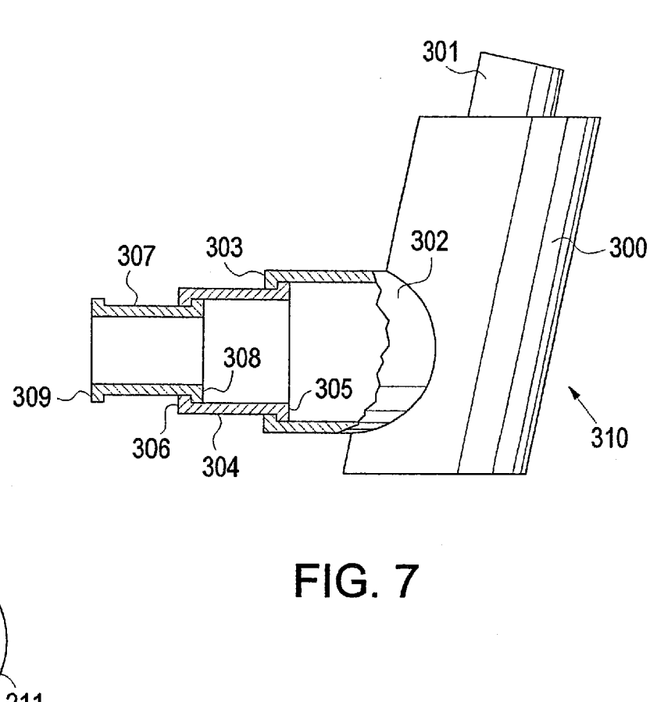
FIG. 7 shows a side partially cut view of another present invention inhaler device with a telescopic spacer retractable within the nozzle.

While FIG. 5 shows a present invention inhaler devise, with the segments connected to the outer nozzle, FIG. 7 shows a present invention inhaler device 310 with the segment being connected to the inner surfaces of the nozzle. Thus, nozzle 302 has stops such as stop 303 and segment 304 has a flange 305 so that segment 304 may slide into and out of nozzle 302 but may not be removed therefrom. Likewise, mouthpiece segment 307 has stops such as stop 309 and a flange which interacts with stop 306 of segment 304 so as to be non-removable slideable therein. Inhaler device 310 has a medication dispensing end 300 with container 301 connected to nozzle 302, as shown.

The present invention devices as shown in FIGS. 5 and 7 both retract so that the space segment and nozzle has a length about equal to or less than the length of the nozzle segment that extends beyond the main housing member.

Figure 8:
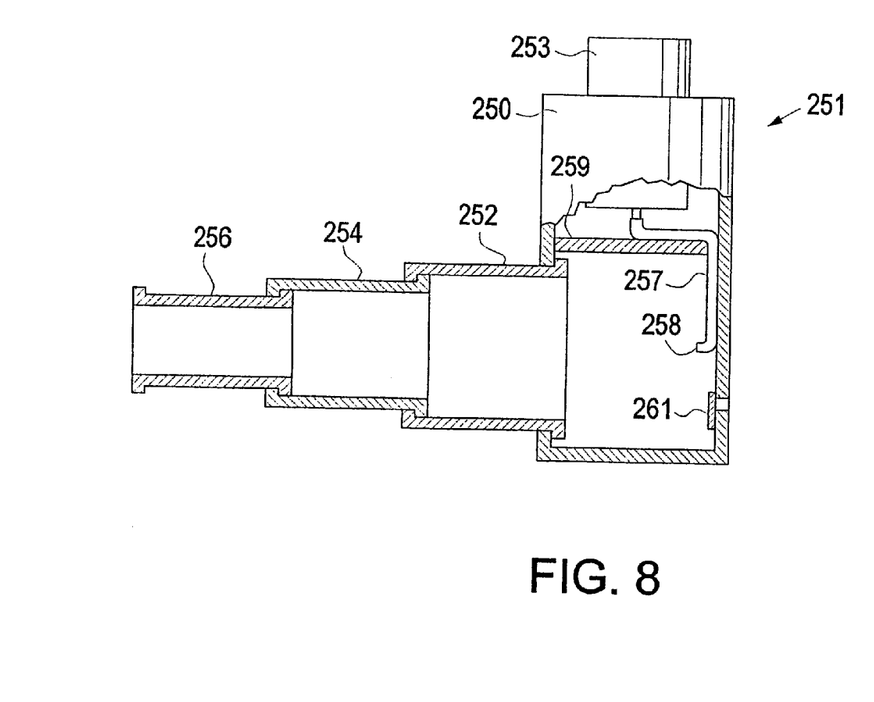
FIGS. 8 and 9 show sideviews of another alternative embodiment of the present invention metered dose inhaler device.
Figure 9:
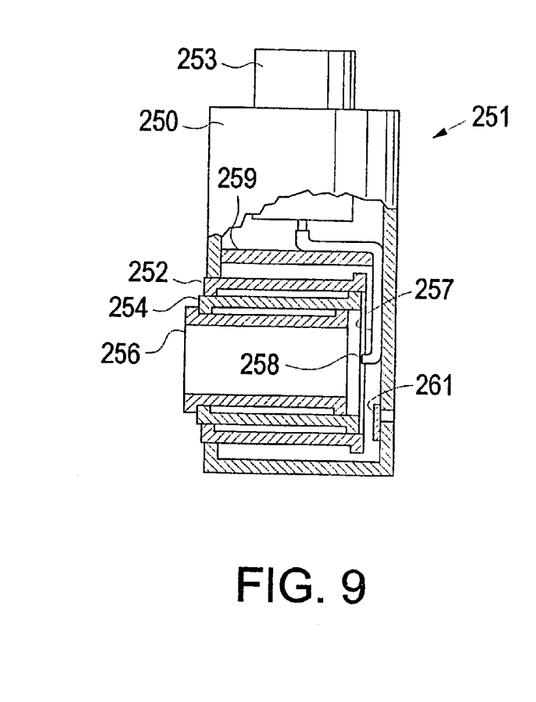

FIGS. 8 and 9 illustrate a present invention inhaler device 251 in its extended and retracted mode, respectively. Both Figures show identical parts identically numbered. Inhaler device 251 has a medicine container 253 with a main housing member 250 and a separator disc 259 that has an orifice through which tube 257 extends. Tube 257 terminates at spray nozzle 258. By locating tube 257 and nozzle 258 as shown, the entire lower space can be used for spacer member storage as shown in FIG. 9. There is a one way valve 261 which functions similarly to valve 211 shown in FIG. 5. In this embodiment, an extendable spacer member is created by three interconnecting telescopic segments 252, 254 and 256. Here at least half of the entire length of the closed spacer member is contained within main housing member 250. In fact, preferred embodiments, at least 60% and most preferably at least 80% of the length of the closed spacer member is contained and stored within the main housing member.

Figure 10:
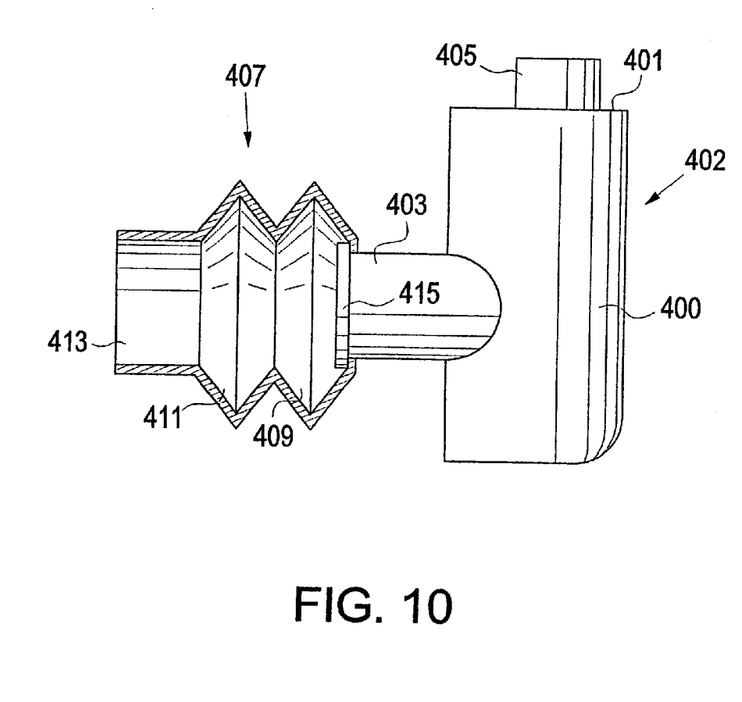
FIGS. 10 and 11 show sideviews of a present invention metered dose inhaler device with a bellows spacer in its extended and retracted modes, respectfully.
Figure 11:
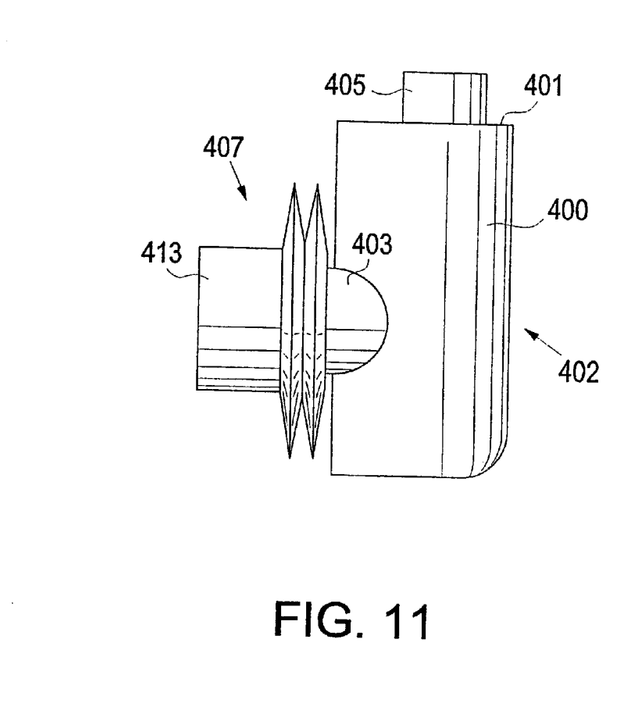

FIGS. 10 and 11 show a present invention inhaler device 402 in its extended and retracted mode, respectively. Referring to both figures wherein identical parts are identically numbered, inhaler device 402 has a medication container receiving section 400 and nozzle 403 with a present invention spacer 407. Inhaler device 402 may include a divider such as is shown in FIG. 6, to prevent medication loss through open top 401. Spacer 407 includes bellows segments 409 and 411 and rigid annular mouthpiece 413. The inner of mouthpiece 14 is slightly greater then flange stop 415 such that when spacer 407 is retracted, mouthpiece 413 fits over nozzle 403, as shown in FIG. 11.

Figure 12:
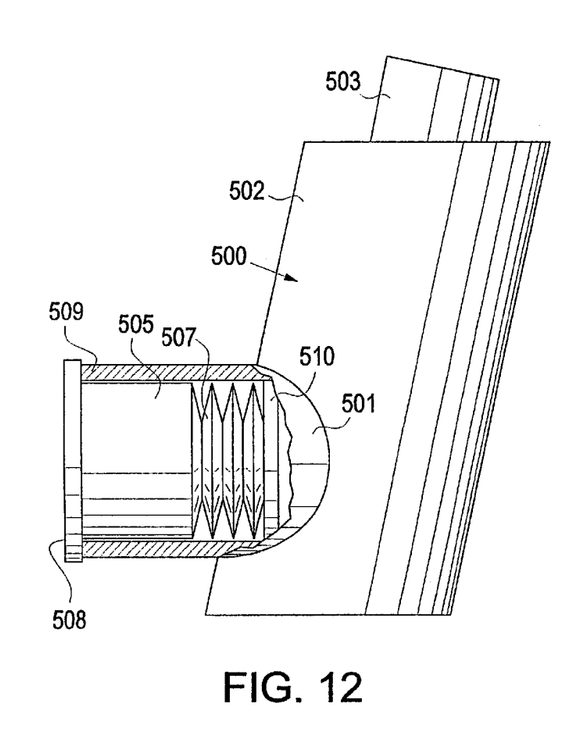
FIG. 12 shows a side partially cut view of a present invention inhaler device with a popoid type spacer contained within the nozzle; and, FIGS. 13 and 14 illustrate open and closed bellows

FIG. 12 shows a present invention inhaler device 500 with nozzle portion 501 and main body 502, with medication container 503 inserted therein. Nozzle portion 501 contains a spacer member with a smaller outer diameter than the inner diameter of nozzle portion 501. In other words, the spacer member is fitted inside nozzle portion 501 so that at least half, and preferably 60%, and most preferably 80%, of the length of the spacer member is contained within said nozzle portion. This spacer has a rigid ring extendable mouthpiece 505 with a flange stop 508 and a set of popoid such segment such as segment 507 and stop end ring 510 so that the spacer may be slid out with stop end ring 510 stopping at stop 509 and then the popoid sections extending further out in accordance particularly with the result achieved as set forth in the discussion of FIGS. 13 through 17 below.

Referring now to FIGS. 13 through 17 there is shown front views of bellows-type expansion-retraction spacer elements and popoid-type expansion-retraction spacer elements. The primary difference is that bellows merely close and open in an accordion fashion, whereas popoids retract by nesting. Both types are to be included within scope of the present invention spacers.

Figure 13:
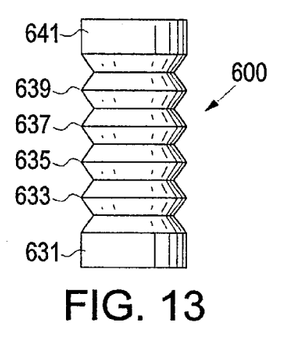
Figure 14:
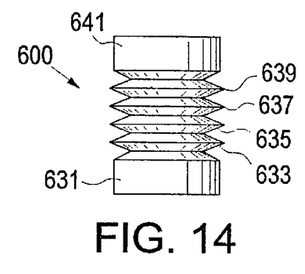

In FIGS. 13 and 14, bellows spacer element 600 is shown in its open and closed (extended and retracted) modes, respectively. Segments 631, 633, 635, 637, 639 and 641 are pulled apart, as shown in FIG. 13. However, in FIG. 14, they are compressed.

Figure 15:
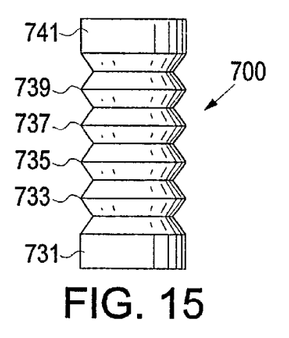
FIGS. 15, 16, and 17 show open, partially closed popoids, all of which are utilized in spacers of the present invention.
Figure 16:
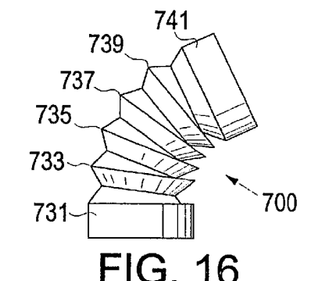
Figure 17:
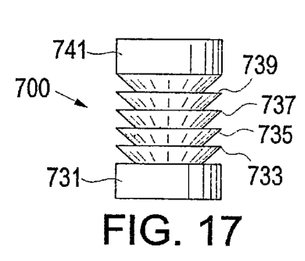

In FIGS. 15, 16 and 17, there is shown a front view of a fully expanded, tilted and fully compressed hollow popoid 700, respectively. As shown in FIG. 2, hollow popoid 700 is fully open and includes end pieces 731 and 741. Therebetween are corrugated segments 733, 735, 737 and 739. They are not part of continuous coil or wire but are, at their widest points, unconnected to one another by any additional or hidden infrastructure. While these corrugated segments are in the fully opened position, they is are symmetrical and in a maximum "stretch" rest position. If ends 731 and 741 were pulled, then they may flex or stretch somewhat, but not significantly. In fact, the position shown in FIG. 15 is relatively rigid and could be relied upon to act as or be a component of an inhaler spacer provided that the thickness of the plastic is adequate to do so and actual tests have shown that these do work.

FIG. 16 shows popoid 700 wherein the right side of each of the corrugated segments have been compressed and the left sides have not been compressed so as to cause a tilt. If only one were compressed, then a smaller angle would be formed, and if only two were compressed then a next larger angle would be formed, and if three were compressed, the angle would get greater, with the maximum angle being created with all of the corrugations being compressed on one side. This would enable an inhaler user to use angles other than straight, relative to the nozzle end of an inhaler, if desired.

FIG. 17 shows popoid 700 wherein the corrugated segments are all fully compressed (retracted mode). No angle results other than a straight line, but the length is substantially shortened due to the folds in corrugated segments after full compression. This rest position, as well as those shown in FIGS. 15 and 16, are positions which will maintain fixed relationships between an inhaler nozzle end and a popoid end as a mouthpiece, and thus, popoid 700 is used accordingly as an inhaler spacer attachment of the present invention. It may be larger enough, i.e. have a large inside diameter, including the end mouthpiece, to fit over the conventional nozzle for maximum compactness or it may be small enough, i.e. a small outer diameter, to fit inside a nozzle.

In these particular embodiments, since the corrugated segments are of equal size and angles, when they are sequentially compressed on one side, the angle between the end of popoid 700 becomes larger sequentially at a fixed multiple of the smallest angle created. On the other hand, if the corrugations were different sizes and/or different angles (created, for example, by the tops or bottoms of each corrugation having varying diameters), then sequential compression of one side of the corrugated segments would result in increasingly larger angles created but they would not be multiples necessarily of the first angle created. While it would seem illogical to create corrugated segments of different sizes or different angles, it should be understood that it is intended that such variations be covered by the present invention, although the discussion will presume corrugations of equal sizes and angles. Similar considerations apply to bellows and to telescopic ring segments used herein.

Obviously, numerous modifications and variations of the present invention are possible in light of the above teachings. For example, the segments used in the spacers need not be circular and in some cases it is desirable. As another example, the present invention device 251 shown in FIG. 8 could have an orifice in the center of separator disc 259 instead of its present arrangement wherein nozzle 258 would be truncated at separator disc 259 without an extended tube. It is therefore understood that within the scope of the appended claims, the invention may be practiced otherwise than as specifically described herein.

What is claimed is:

1. In a metered dosage inhaler device having a main housing member for receiving and dispensing inhalation medication, said main housing member being hollow, and having an aerosol medication container insertion end and a central axis of direction of insertion of an aerosol medication container and having a nozzle portion for spraying medication into a mouth of a user, said nozzle portion extending away from said central axis, wherein said nozzle portion includes a nozzle segment that is exterior from said main housing member and has a defined length L, and has an orifice with outer surfaces and inner surfaces, the improvement which comprises:

a spacer member, said spacer member being fitted on said nozzle segment and adapted to move outwardly and inwardly relatively to said nozzle segment, said spacer member being hollow and being located about said outer surfaces of said nozzle segment, said spacer member including a plurality of moveable segments, each of said moveable segments being interconnected with one another, said spacer member having an open extended position wherein said moveable segments are extended relative to one another to create an elongated spacer member, wherein an extended most moveable segment is a mouthpiece segment, and said spacer member having a closed, collapsed position wherein said moveable segments are all located about said nozzle segment, including said mouthpiece segment, so as to have a total length about equal to or less than said nozzle segment length L, so as to preserve significant compactness when said spacer is moved inwardly relative to said nozzle segment, and so as to eliminate protrusion beyond said nozzle segment.

2. The device of claim 1 wherein said moveable segments are interlocking collapsible, telescopic rings.

3. The device of claim 2 wherein said interlocking telescopic rings are of decreasing internal diameter, such that, when in its open, extended position, a smallest internal diameter ring is furthest away from said nozzle segment and is said mouthpiece segment.

4. The device of claim 1 wherein said moveable segments are bellows segments.

5. The device of claim 1 wherein said moveable segments are popoid segments.

6. The device of claim 1, which further comprises:

a divider wafer, said divider wafer being positioned within said main housing member between said container insertion end and said nozzle portion so as to inhibit air movement from said nozzle portion to said container insertion end.

7. The device of claim 6 wherein said divider wafer includes a one-way valve to permit air flow from said container insertion end of said main housing member to said nozzle portion and not vice-versa.

8. The device of claim 7 wherein said moveable segments are interlocking collapsible, telescopic rings.

9. The device of claim 7 wherein said moveable segments are bellows segments.

10. The device of claim 7 wherein said moveable segments are popoid segments.

11. In a metered dosage inhaler device having a main housing member for receiving and dispensing inhalation medication, said main housing member being hollow, and having an aerosol medication container insertion end and a central axis of direction of insertion of an aerosol medication container and having a nozzle portion for spraying medication into a mouth of a user, said nozzle portion extending away from said central axis, wherein said nozzle portion includes a nozzle segment that is exterior from said main housing member and has a defined length L, and has an orifice with outer surfaces and inner surfaces, the improvement which comprises:

a spacer member fitted on said nozzle segment and adapted to move outwardly and inwardly relatively to said nozzle segment, said spacer member being hollow and being located within said inner surfaces of said nozzle segment, said spacer member including a plurality of moveable segments, each of said moveable segments being interconnected with one another, said spacer member having an open extended position wherein said moveable segments are extended relative to one another to create an elongated spacer member, wherein an extended most moveable segment is a mouthpiece segment, and said spacer having a closed, collapsed position wherein said moveable segments are all located about said nozzle segment, including said mouthpiece segment, so as such that at least half of the length of said spacer member, in its closed position is contained within said nozzle portion so as to preserve significant compactness.

12. The device of claim 11 wherein said moveable segments are interlocking collapsible, telescopic rings.

13. The device of claim 12 wherein said interlocking telescopic rings are of decreasing internal diameter, such that, when in its open, extended position, a smallest internal diameter ring is furthest away from said nozzle segment and is said mouthpiece segment.

14. The device of claim 11 wherein said moveable segments are bellows segments.

15. The device of claim 11 wherein said moveable segments are popoid segments.

16. The device of claim 11, which further comprises:

a divider wafer, said divider wafer being positioned within said main housing member between said container insertion end and said nozzle portion so as to inhibit air movement from said nozzle portion to said container insertion end.

17. The device of claim 16 wherein said divider wafer includes a one-way valve to permit air flow from said container insertion end of said main housing member to said nozzle portion and not vice-versa.

18. The device of claim 17 wherein said moveable segments are selected from the group consisting of interlocking collapsible, telescopic rings, bellow segments and popoid segments.

19. In a metered dosage inhaler device having a main housing member for receiving and dispensing inhalation medication, said main housing member being hollow, and having an aerosol medication container insertion end and a central axis of direction of insertion of an aerosol medication container and having a nozzle opening for spraying medication into a mouth of a user, said nozzle opening extending away from said central axis, the improvement which comprises:

a spacer member fitted into said nozzle opening and said main housing member, and adapted to move outwardly and inwardly relatively to said nozzle opening, said spacer member being hollow and being located within said nozzle opening, said spacer member including a plurality of moveable segments, each of said moveable segments being interconnected with one another, said spacer member having an open extended position wherein said moveable segments are extended relative to one another to create an elongated spacer member, wherein an extended most moveable segment is a mouthpiece segment, and said spacer having a closed, collapsed position wherein said moveable segments are substantially located within said main housing member such that at least half of the length of said spacer member is located within said main housing member, so as to preserve significant compactness when said spacer member is moved inwardly relative to said nozzle.

20. The device of claim 19 wherein said moveable segments are selected from the group consisting of interlocking collapsible, telescopic rings, bellow segments and popoid segments.

\* \* \* \* \*